United States Patent
Monath et al.

(10) Patent No.: US 6,682,883 B1
(45) Date of Patent: Jan. 27, 2004

(54) DIAGNOSIS OF FLAVIVIRUS INFECTION

(75) Inventors: Thomas P. Monath, Harvard, MA (US); Richard D. Nichols, Jr., Burlington, MA (US)

(73) Assignee: Acambis, Inc., Cambridge, MA (US)

( * ) Notice: Subject to any disclaimer, the term of this patent is extended or adjusted under 35 U.S.C. 154(b) by 0 days.

(21) Appl. No.: 09/910,647

(22) Filed: Jul. 19, 2001

(51) Int. Cl.$^7$ .............................. C12Q 1/70; C12Q 1/02
(52) U.S. Cl. ........................ 435/5; 435/7.1; 435/7.21; 435/173.3; 435/235.1; 435/236; 435/239
(58) Field of Search ........................... 435/5, 7.1, 7.21, 435/173.3, 235.1, 236, 239

(56) References Cited

U.S. PATENT DOCUMENTS 6,184,024 B1    2/2001  Lai et al.

FOREIGN PATENT DOCUMENTS

| WO | WO 93/06214 | | 4/1993 |
| WO | WO 98/37911 | * | 9/1998 |
| WO | WO 01/39802 A1 | | 6/2001 |

OTHER PUBLICATIONS

Morley et al. Vet. Micro. Vol 45 (1) pp. 81–92.*
Bray et al., "Construction of Intertypic Chimeric Dengue Viruses by Substitution of Structural Protein Genes," Proc. Natl. Acad. U.S.A. 88:10342–10346 (1991).
Calisher et al., "Antigenic Relationships Between Flaviviruses as Determined by Cross–neutralization Tests with Polyclonal Antisera," Journal of General Virology 70:37–43 (1989).
Chambers et al., "Yellow Fever/Japanese Encephalitis Chimeric Viruses: Construction and Biological Properties," Journal of Virology 73:3095–3101 (1999).
Duarte dos Santos et al., "Complete Nucleotide Sequence of Yellow Fever Virus Vaccine Strains 17DD and 17D–213," Virus Research 35:35–41 (1995).
Galler et al., "Genetic Variability Among Yellow Fever Virus 17D Substrains," Vaccine 16:1–5 (1998).
Marchevsky et al., "Phenotypic Analysis of Yellow Fever Virus Derived from Complementary DNA," American J. Tropical Medicine & Hygiene 52:75–80 (1995).
Monath et al., "Chimeric Yellow Fever Virus 17D–Japanese Encephalitis Virus Vaccine: Dose–Response Effectiveness and Exteneded Safety Testing in Rhesus Monkeys," Journal of Virology 74:1742–1751 (2000).
Rice et al., "Transcription of Infectious Yellow Fever RNA from Full–Length cDNA Templates Produced by In Vitro Ligation," The New Biologist 1:285–296 (1989).
Venugopal et al., "Towards a New Generation of Flavivirus Vaccines," Vaccines 12:966–975 (1994).
U.S.S.N. 09/007,664, Chambers et al., "Chimeric Flavivirus Vaccines," filed: Jan. 15, 1998.
U.S.S.N. 09/121,587, Chambers et al., "Chimeric Flavivirus Vaccines," filed: Jul. 23, 1998.
U.S.S.N. 09/452,638, Chambers et al., "Chimeric Flavivirus Vaccines," filed: Dec. 1, 1999.

* cited by examiner

*Primary Examiner*—James Housel
*Assistant Examiner*—Myron G. Hill
(74) *Attorney, Agent, or Firm*—Clark & Elbing LLP

(57) ABSTRACT

The invention provides methods and kits for use in diagnosing flavivirus infection.

6 Claims, No Drawings

DIAGNOSIS OF FLAVIVIRUS INFECTION

FIELD OF THE INVENTION

This invention relates to methods of diagnosing flavivirus infection.

BACKGROUND OF THE INVENTION

There are approximately 70 members of the flavivirus genus, a group of viruses that are antigenically very closely related, and distinguishable only by a specific neutralization test method (Calisher et al., J. Gen. Virol. 70:37–43, 1989). Approximately half of the 70 flaviviruses pose current or potential threats to public health. For example, Japanese encephalitis virus is a significant public health problem, involving millions of persons at risk in the Far East. Dengue virus, causing an estimated annual incidence of 100 million cases of primary dengue fever and over 450,000 cases of dengue hemorrhagic fever worldwide, has emerged as the single most important arthropod-transmitted human disease. In addition, West Nile virus, which causes febrile illness, occasionally complicated by acute encephalitis, is widely distributed throughout Africa, the Middle East, the former Soviet Union, and parts of Europe, and has recently become a concern in the eastern United States.

Other flaviviruses continue to cause endemic diseases of variable nature and have the potential to emerge into new areas as a result of changes in climate, vector populations, and environmental disturbances caused by human activity. These flaviviruses include, for example, St. Louis encephalitis virus, which causes sporadic, but serious, acute disease in the midwest, southeast, and western United States; Murray Valley encephalitis virus, which causes endemic nervous system disease in Australia; and Tick-borne encephalitis virus, which is distributed throughout the former Soviet Union and eastern Europe, where its Ixodes tick vector is prevalent and responsible for a serious form of encephalitis in those regions.

Hepatitis C virus (HCV) is another member of the flavivirus family, with a genome organization and a replication strategy that are similar, but not identical, to those of the flaviviruses mentioned above. HCV is transmitted mostly by parenteral exposure and congenital infection, is associated with chronic hepatitis that can progress to cirrhosis and hepatocellular carcinoma, and is a leading cause of liver disease requiring orthotopic transplantation in the United States.

Because of the impact of flaviviruses on worldwide public health, it is important that there be diagnostic tests that can be used to specifically and easily detect flavivirus infection in samples, in a variety of hospital or laboratory settings. Several types of antibody-based tests have been used to detect flavivirus infections, including enzyme-linked immunoassays (ELISAs), complement-fixation assays, hemagglutination-inhibition assays (HAIs), and neutralization assays. The first three assays listed are advantageous because they can employ inactivated antigens. This is important because work with live flaviviruses generally must be carried out in Biosafety Level 3 (BSL3) laboratories, which most pubic health and diagnostic facilities do not have. However, these assays are not without disadvantages. For example, these assays measure antibody binding at epitopes that are cross-reactive among different flaviviruses, making it very difficult to determine which particular flavivirus may be present in a sample. This is especially important in settings in which multiple flaviviruses co-exist. For example, in the United States, both St. Louis encephalitis and West Nile virus co-exist. Indeed, the original (1999) epidemic of West Nile encephalitis in New York was initially misdiagnosed at St. Louis encephalitis, because antibodies in patient's blood cross-reacted with St. Louis encephalitis in ELISAs. In Australia, Murray Valley encephalitis, Japanese encephalitis, West Nile, and Kokobera viruses co-circulate and can cause diagnostic confusion. Similar considerations apply throughout Asia and Latin America, where multiple flaviviruses infect humans and animals.

The fourth assay listed above, the neutralization assay, overcomes this shortcoming of the other assays, in that it measures only neutralization epitopes, which vary between different flaviviruses. In fact, the 70 species within the flavivirus genus are distinguished based on differences in the neutralization test. Unfortunately, however, neutralization tests, which provide the specificity required to identify a particular flavivirus, cannot be used in most settings, because utilization of live virus, and thus BSL3 facilities, are required for these tests. Thus, the field would benefit from the development of a test that has the specificity of a neutralization test, but that would not require the use of a BSL3 facility.

Flaviviruses are members of a family of small, enveloped positive-strand RNA viruses. Flavivirus proteins are produced by translation of a single, long open reading frame to generate a polyprotein, and a complex series of post-translational proteolytic cleavages of the polyprotein by a combination of host and viral-proteases, to generate mature viral proteins (Amberg et al., J. Virol. 73:8083–8094, 1999; Rice, "Flaviviridae," In *Virology*, Fields (ed.), Raven-Lippincott, New York, 1995, Volume I, p. 937). The virus structural proteins are arranged in the order C-prM-E, where "C" is capsid, "prM" is a precursor of the viral envelope-bound M protein, and "E" is the envelope protein. These proteins are present in the N-terminal region of the polyprotein, while the non-structural proteins (NS1, NS2A, NS2B, NS3, NS4A, NS4B, and NS5) are located in the C-terminal region of the polyprotein. The amino termini of prM, E, NS1, and NS4B are generated by host signalase cleavage within the lumen of the endoplasmic reticulum (ER), while most cleavages within the non-structural region are mediated by a viral protease complex known as NS2B-NS3 (Rice, supra). In addition, the NS2B-NS3 protease complex is responsible for mediating cleavages at the C terminus of both the C protein and the NS4A protein (Amberg et al., supra).

SUMMARY OF THE INVENTION

The invention provides methods of specifically detecting antibody against a predetermined virus that is present in a biological sample. The methods involve: (a) providing a chimeric virus having the following characteristics: (i) the chimeric virus includes nucleic acid sequences derived from two different viruses, one of which is the predetermined virus, the other being a flavivirus that is used as the chimera backbone; (ii) the chimeric virus is capable of replicating; (iii) the chimeric virus is substantially neutralized by antibodies to the predetermined virus and is not neutralized, or is neutralized to a lesser degree, by antibodies to other viruses, including the flavivirus used as the chimera backbone; (iv) the chimeric virus is attenuated compared to the predetermined virus; and (v) the chimeric virus may be safely manipulated in the laboratory at a Biosafety level that is lower than that required for the predetermined virus; (b) contacting the biological sample with the chimeric virus under neutralizing conditions; and (c) determining the presence or amount of infectious virus remaining following step (b) as an inverse measure of antibody against the predetermined virus that is present in the biological sample.

Step (c) of this method can involve, for example, inoculating a mammal with the sample-contacted chimeric virus, and then determining virus-induced illness or mortality in the mammal as a measure of non-neutralized infectious chimeric virus. Alternatively, step (c) can involve inoculating a cell culture with the sample-contacted chimeric virus, and then determining cytopathic effects, absence of metabolic activity, absence of uptake of vital dyes, or plaque formation as a measure of non-neutralized infectious chimeric virus.

The chimeric virus can include a backbone (e.g., yellow fever 17D virus) in which one or more structural genes (e.g., prM-E genes) have been replaced by the corresponding structural genes of the predetermined virus. The predetermined virus can be a flavivirus, for example, a mosquito-borne virus selected from the group consisting of Japanese encephalitis, Dengue (serotype 1, 2, 3, or 4), Yellow fever, Murray Valley encephalitis, St. Louis encephalitis, West Nile, Kunjin, Rocio encephalitis, and Ilheus viruses; a tick-borne flavivirus selected from the group consisting of Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses. All of these viruses are members of the family Flaviviridae. The principal underlying the use of chimeric viruses for diagnostic tests is the complete replacement of the envelope genes of the vector backbone (e.g., yellow fever 17D), so that the only remaining neutralization epitopes are those of the predetermined virus.

Genes containing neutralization epitopes or neutralization epitopes themselves from other members of the family Flaviviridae, but outside the genus Flavivirus (e.g., viruses from the Hepacivirus genus (e.g., a Hepatitis C virus) or Pestivirus genus (e.g., Bovine viral diarrhea virus), or from viruses outside the family Flaviviridae can also be used as donors for construction of chimeric viruses, which in turn may be used for detection of antibodies by neutralization test. For example, genes or epitopes from dangerous pathogens such as Lassa virus, Ebola virus, or Marburg virus could be inserted into a suitable backbone from an attenuated virus (e.g., yellow fever 17D), yielding a chimeric virus that may be safely manipulated in the laboratory for detection of neutralizing antibodies. In these cases, part of the envelope genes of the vector backbone (e.g., yellow fever 17D), would remain in the chimeric virus. For use in diagnostic tests, the vector virus (e.g., yellow fever 17D) would be used as a control to ensure specificity of the reaction to the gene or epitope of interest.

The invention also provides kits that can be used to carry out the methods described herein. The kits can contain a chimeric virus (see above) that includes structural proteins (e.g., prM and E proteins) of a predetermined virus, the presence of which in a sample can be tested for by use of the kit, or can include a nucleic acid molecule corresponding to the genome of such a chimeric virus. The kit can also include, for example, neutralizing antibodies against the predetermined virus, additional controls, buffers that can be used in the assays, instructions for carrying out the diagnostic methods described herein, vessels in which various steps of the method are carried out (e.g., tubes and/or trays). The kits of the invention are described in further detail below.

The invention provides several advantages. For example, as is noted above, previous assays used for diagnosing flavivirus infection employed either inactive viral antigens, and thus lacked the specificity required to distinguish between closely related flaviviruses, or employed live virus in neutralization assays and, thus, while providing high levels of specificity, required the use of BSL3 facilities. The present invention, involving the use of attenuated viruses, enables the use of the more sensitive and specific neutralization assay, but does not require the use of BSL3 facilities. The specificity of the methods of the invention enables medical professionals to pursue a course of treatment that is specific for the particular disease to be treated in a subject. The methods of the invention also enable public health and environmental professionals to track which particular viruses may be present in animal (e.g., mammal or bird) populations. In addition, these methods can be carried out in facilities having a lower Biosafety level (e.g., BSL2) than would be required for carrying out similar assays using wild type virus (e.g., BSL3 facilities).

Other features and advantages of the invention will be apparent from the following detailed description and the claims.

DETAILED DESCRIPTION

The invention provides sensitive and specific methods that can be used to detect viruses, such as flaviviruses. These methods can be used, for example, in the diagnosis of viral infections of humans, domestic livestock, and wild animals, and depend on the accurate measurement of antibodies against viruses in samples such as blood or cerebrospinal fluid. The methods of the invention can also be used for surveillance of virus infection by testing samples from wild birds and other animals. Further, the methods of the invention can be used for assessing the efficacy of a vaccination regimen against viral infection.

The methods of the invention involve the use of live, infectious, attenuated chimeric viruses in neutralization assays. Because the viruses are attenuated, facilities having a Biosafety level (e.g., BSL2) that is lower than that which would be required for use with the corresponding wild type virus (e.g., BSL3) can be used. (See, e.g., Richmond et al., "Biosafety in Microbiological and Biomedical Laboratories," U.S. Department of Health and Human Services, CDC/NIH, $3^{rd}$ Edition, U.S. Government Printing Office, Washington, D.C. (1993), for a discussion of Biosafety levels.) However, the attenuated chimeric viruses replicate sufficiently to be useful in neutralization tests. Also, in employing a neutralization assay, which is the most specific and sensitive test that can be used, the methods of the invention enable the determination of precisely which virus may be present in a sample. The details of the methods of the invention and the chimeric viruses that are used in these methods are described further as follows.

Chimeric viruses that can be used in the invention consist of a flavivirus (i.e., a backbone flavivirus) in which a structural protein (or proteins) has been replaced with a corresponding structural protein (or proteins) of a second virus (i.e., a test or a predetermined virus, such as a flavivirus). For example, the chimeras can consist of a backbone flavivirus in which the prM and E proteins of the flavivirus have been replaced with the prM and E proteins of the second, test virus. Because neutralization epitopes are found predominantly in these structural proteins, the use of such chimeric viruses in neutralization assays enables the testing of samples for antibodies that are specific for the second, test virus, from which the inserted proteins are derived. Thus, to test a sample for a particular virus, according to the invention, a chimeric virus including structural proteins (e.g., prM and E proteins) from that virus should be used.

The chimeric viruses that are used in the invention can be made from any combination of viruses, provided that, as is mentioned above, the virus that is being tested for is the source of the inserted structural protein(s). Examples of particular flaviviruses that can be used in the invention, as backbone or test viruses, include mosquito-borne flaviviruses, such as Japanese encephalitis, Dengue (serotypes 1–4), Yellow fever, Murray Valley encephalitis, St. Louis encephalitis, West Nile, Kunjin, Rocio encephalitis, and Ilheus viruses; tick-borne flaviviruses, such as Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses; as well as viruses from the Hepacivirus genus (e.g., Hepatitis C virus). Additional viruses that can be used as the source of inserted structural proteins include viruses from the Pestivirus genus (e.g., Bovine diarrhea virus), and other viruses, such as Lassa, Ebola, and Marburg viruses. Details of making chimeric viruses that can be used in the invention are provided, for example, in U.S. patent application Ser. Nos. 09/007,664, 09/121,587, and 09/452,638; International applications PCT/US98/03894 and PCT/US00/32821; and Chambers et al., J. Virol. 73:3095–3101, 1999, each of which is incorporated by reference herein in its entirety.

A specific example of a chimeric virus that can be used in the invention is the yellow fever human vaccine strain, YF17D, in which the prM and E proteins have been replaced with prM and E proteins of another flavivirus, such as Japanese encephalitis virus, West Nile virus, St. Louis encephalitis virus, Murray Valley encephalitis virus, a Dengue virus, or any other flavivirus, such as one of those listed above. For example, the following chimeric flaviviruses, which were deposited with the American Type Culture Collection (ATCC) in Manassas, Va., U.S.A. under the terms of the Budapest Treaty and granted a deposit date of Jan. 6, 1998, can be used in the invention: Chimeric Yellow Fever 17D/Dengue Type 2 Virus (YF/DEN-2; ATCC accession number ATCC VR-2593) and Chimeric Yellow Fever 17D/Japanese Encephalitis SA14-14-2 Virus (YF/JE A1.3; ATCC accession number ATCC VR-2594).

As is noted above, the most sensitive and specific test for antibodies to flaviviruses is the neutralization test, in which a test sample (e.g., a blood sample, such as serum, or cerebrospinal fluid) from an affected subject (e.g., a human patient or an animal) is mixed with a flavivirus and the sample/virus mixture is tested for residual virus infectivity. Neutralization of infectivity by antibody present in the sample is indicative of infection with the virus in question.

The neutralization tests of the invention, employing chimeric viruses, can be performed using any of a variety of standard methods that are well known in this art. All of these methods involve mixing a test sample (e.g., a blood sample, such as serum, or a cerebrospinal fluid sample) from a subject with a chimeric virus or a panel of chimeric viruses, and then testing the mixture for the presence of residual (i.e., un-neutralized) infectious virus.

In one example of a test that can be used in the invention, a test sample is mixed with an amount of chimeric virus that has been shown to be neurovirulent in an animal model system, such as a mouse system (e.g., ICR mice, Taconic Farms, Germantown, N.Y.). Preferably, prior to mixing with the chimeric virus, the sample is inactivated by, e.g., heating at 56° C. for 30 minutes, and then is mixed with the chimeric virus in serial twofold dilutions. Mice (e.g., infant mice) are inoculated intracranially under isofluorane anesthesia with mixed samples or, as a control, chimeric virus that has not been mixed with a test sample, and monitored for illness and death. Detection of a decreased level of morbidity or mortality in a test mouse indicates the presence of neutralizing antibodies in the test sample. As is discussed above, antibodies identified in this manner are specific for the virus from which the inserted structural proteins have been derived.

In another example of a test that can be used in the invention, the mixture of test sample and chimeric virus, as described above, is inoculated into a cell culture system (e.g., Vero cells) and the effect of any antibodies present in the test sample on the cytopathogenicity of the virus is determined relative to a control. Residual infectious virus can be detected by analysis of cytopathic effect or plaque formation, as well as by use of techniques such as immunofluorescence, immunocytochemistry, ELISA, metabolic inhibition, or the polymerase chain reaction (e.g., Taq-man PCR). Details of the above-described methods are provided, for example, in Monath et al., J. Virol. 74(4):1742–1751, 2000.

To illustrate the example described above, patients infected with Japanese encephalitis or yellow fever viruses were tested before and 30 days after infection for the presence of neutralizing antibodies to both viruses. ChimeriVax™-JE and yellow fever 17D viruses were used as the diagnostic reagents in the neutralization tests. The method used was a plaque-reduction neutralization test performed in Vero cell cultures, and using the constant serum-varying virus technique. Seroconversion is defined as a $\log_{10}$ neutralization index (LNI) of $\geq 0.7$ (Mason et al., Appl. Microbiol. 23:908, 1972). The LNI is calculated as the $\log_{10}$ difference in virus titer of a mixture of serum and virus between baseline (pre-immunization) and post-immunization samples. The post-vaccination serum from a patient who does not seroconvert will have a LNI<0.7 compared to his/her pre-vaccination serum. The results of tests on 12 subjects infected with a JE virus and 6 patients infected with a yellow fever virus are shown in the following Table. All 12 patients infected with a JE virus developed neutralizing antibodies against ChimeriVax™-JE virus, but had no detectable antibodies against yellow fever virus. Similarly, all 6 subjects infected with a yellow fever virus developed neutralizing antibodies against yellow fever, but none had antibodies against ChimeriVax™-JE. These results show that the neutralization test was highly specific for detecting antibodies against the infecting viral species, even though ChimeriVax™ contains the capsid and nonstructural proteins of yellow fever virus.

The invention also includes kits that can be used to carry out the methods described herein. These kits can include any of the materials that would be required to carry out the diagnostic assays of the invention, as described herein, as well as instructions for carrying out these methods. For example, a kit according to the invention can include a preparation of a particular chimeric virus (see, e.g., above) that includes structural proteins (e.g., prM and E proteins) from a virus that is to be tested for using the kit, as well as neutralizing antibodies against the virus to be used in a control assay. The viral material in the kit can be present in separate vessels, such as tubes or plates in a well, to which a sample (or a series of sample dilutions) is added. Alternatively, the viral material can be present in a single vessel from which appropriate amounts of viral material is obtained, as needed. Also, the kits can include material for testing for one virus or several different viruses, and can include, optionally, buffers that can be used in the assays. Further, rather than including the chimeric viruses themselves, the kits of the invention can include nucleic acid molecules corresponding to the viral genomes, which can be used to generate the chimeric viruses in appropriate cell culture systems. For example, the kits can include DNA corresponding to the viral genomes of a chimera and materials for transcribing the DNA (e.g., NTPs and the appropriate RNA polymerase).

TABLE

Specificity of the neutralizing antibody response using ChimeriVax ™-JE as a diagnostic reagent

| Subject | Infecting virus | Day after infection | Virus used in neutralization test | |
|---|---|---|---|---|
| | | | ChimeriVax-JE | Yellow fever |
| 105 | Japanese encephalitis | 1 | 0.0 | 0 |
| | | 31 | 3.2 | 0 |
| 106 | | 1 | 0.0 | 0 |
| | | 31 | 1.9 | 0 |
| 107 | | 1 | 0.0 | 0 |
| | | 31 | 1.0 | 0 |
| 110 | | 1 | 0.0 | 0 |
| | | 31 | 0.9 | 0 |
| 113 | | 1 | 0.0 | 0 |
| | | 31 | 0.8 | 0 |
| 118 | | 1 | 0.0 | 0 |
| | | 31 | 1.5 | 0 |
| 101 | | 1 | 0.0 | 0 |
| | | 31 | 0.7 | 0 |
| 104 | | 1 | 0.0 | 0 |
| | | 31 | 1.1 | 0 |
| 111 | | 1 | 0.0 | 0 |
| | | 31 | 1.2 | 0 |
| 112 | | 1 | 0.0 | 0 |
| | | 31 | 0.7 | 0 |
| 114 | | 1 | 0.0 | 0 |
| | | 31 | 2.5 | 0 |
| 117 | | 1 | 0.0 | 0 |
| | | 31 | 2.1 | 0 |
| 102 | Yellow fever | 1 | 0.0 | 0 |
| | | 31 | 0.0 | 3.7 |
| 103 | | 1 | 0.0 | 0 |
| | | 31 | 0.2 | 3.4 |
| 108 | | 1 | 0.0 | 0 |
| | | 31 | 0.0 | 4.3 |
| 109 | | 1 | 0.0 | 0 |
| | | 31 | 0.5 | 4.3 |
| 115 | | 1 | 0.0 | 0 |
| | | 31 | 0.0 | 4.4 |
| 116 | | 1 | 0.0 | 0 |
| | | 31 | 0.2 | 3.8 |

All references cited above are hereby incorporated by reference herein in their entirety. The invention has been described above in relation to particular embodiments, which are not intended to be limiting of the invention in any manner. Other embodiments are within the following claims.

What is claimed is:

1. A method of diagnosing a mammal as being infected with a predetermined flavivirus by specifically detecting antibodies against said flavivirus in a biological test sample from said mammal, said method comprising the steps of:
   (a) providing a chimeric virus having the following characteristics:
      (i) the chimeric virus comprises nucleic acid sequences derived from two different viruses, one nucleic acid sequence is from said predetermined flavivirus structural genes prM-E, the other being a flavivirus that is used as the chimera backbone;
      (ii) the chimeric virus is capable of replicating;
      (iii) the chimeric virus is substantially neutralized by antibodies to said predetermined flavivirus and is not substantially neutralized by antibodies to other viruses, including the flavivirus used as the chimera backbone;
      (iv) the chimeric virus is attenuated compared to said predetermined flavivirus; and
      (v) the chimeric virus may be safely manipulated in the laboratory at a Biosafety level that is lower than that required for said predetermined flavivirus;
   (b) providing a biological test sample from said mammal, wherein the presence of said antibodies against said predetermined flavivirus in said sample is not known;
   (c) contacting said biological sample with said chimeric virus under neutralizing conditions; and
   (d) determining the presence or amount of infectious virus remaining following step (c), wherein neutralization of infectivity of said chimeric virus by said antibodies in said test sample is a measure of antibodies against said predetermined flavivirus that are present in said biological sample and identifies the mammal as being infected with said virus.

2. The method of claim 1, wherein step (d) involves inoculating a mammal with the sample-contacted chimeric virus, and then determining virus-induced illness or mortality in said mammal as a measure of non-neutralized infectious chimeric virus.

3. The method of claim 1, wherein step (d) involves inoculating a cell culture with the sample-contacted chimeric virus, and then determining cytopathic effects, absence of metabolic activity, absence of uptake of vital dyes, or plaque formation as a measure of non-neutralized infectious chimeric virus.

4. The method of claim 1, wherein said flavivirus backbone is that of yellow fever 17D virus.

5. The method of claim 1, wherein said predetermined flavivirus is a mosquito-borne flavivirus selected from the group consisting of Japanese encephalitis, Dengue (serotype 1, 2, 3, or 4), Yellow fever, Murray Valley encephalitis, St. Louis encephalitis, West Nile, Kunjin, Rocio encephalitis, and Ilheus viruses.

6. The method of claim 1, wherein said predetermined flavivirus is a tick-borne flavivirus selected from the group consisting of Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses.

* * * * *